US010124020B2

(12) United States Patent
Huzinec et al.

(10) Patent No.: US 10,124,020 B2
(45) Date of Patent: Nov. 13, 2018

(54) COMESTIBLE CONTAINING FINELY GROUND DEMULCENT

(71) Applicant: THE HERSHEY COMPANY, Hershey, PA (US)

(72) Inventors: Robert J. Huzinec, Hummelstown, PA (US); Gagan Mongia, Hershey, PA (US); Mahesh Venkatachalam, Harrisburg, PA (US); Thomas J. Carroll, Mechanicsburg, PA (US); Jordana Langiotti Swank, Hamburg, PA (US); Pamela Gesford, Harrisburg, PA (US)

(73) Assignee: THE HERSHEY COMPANY, Hershey, PA (US)

( * ) Notice: Subject to any disclaimer, the term of this patent is extended or adjusted under 35 U.S.C. 154(b) by 0 days.

(21) Appl. No.: 14/654,653

(22) PCT Filed: Apr. 17, 2014

(86) PCT No.: PCT/US2014/034495
§ 371 (c)(1),
(2) Date: Jun. 22, 2015

(87) PCT Pub. No.: WO2014/172539
PCT Pub. Date: Oct. 23, 2014

(65) Prior Publication Data
US 2015/0342983 A1 Dec. 3, 2015

Related U.S. Application Data

(60) Provisional application No. 61/813,209, filed on Apr. 18, 2013.

(51) Int. Cl.
A61K 31/732 (2006.01)
A23G 3/36 (2006.01)
A23G 3/50 (2006.01)
A23G 3/54 (2006.01)
A61K 9/00 (2006.01)
A61K 9/20 (2006.01)
A61K 45/06 (2006.01)

(52) U.S. Cl.
CPC ............ A61K 31/732 (2013.01); A23G 3/36 (2013.01); A23G 3/50 (2013.01); A23G 3/54 (2013.01); A61K 9/0056 (2013.01); A61K 9/2018 (2013.01); A61K 45/06 (2013.01)

(58) Field of Classification Search
CPC .... A61K 9/2018; A61K 45/06; A61K 31/732; A61K 9/0056; A61K 2300/00; A23G 3/50; A23G 3/54; A23G 3/36
See application file for complete search history.

(56) References Cited

U.S. PATENT DOCUMENTS

| 3,020,164 | A | * | 2/1962 | Forkner | A21D 2/18 426/103 |
| 4,565,702 | A | * | 1/1986 | Morley | A23G 3/48 426/302 |
| 4,686,106 | A | * | 8/1987 | Ehrlich | A23L 1/0524 426/577 |
| 5,718,969 | A | * | 2/1998 | Sewall | A23D 7/0056 426/573 |
| 7,211,283 | B2 | | 5/2007 | Jones | |
| 8,362,036 | B2 | | 1/2013 | Jones | |
| 2003/0224090 | A1 | | 12/2003 | Pearce et al. | |
| 2005/0118311 | A1 | | 6/2005 | Best et al. | |
| 2007/0087053 | A1 | * | 4/2007 | Hayward | A61K 9/0056 424/466 |
| 2010/0221342 | A1 | | 9/2010 | Jones | |
| 2011/0039945 | A1 | * | 2/2011 | Chen | A61K 9/1652 514/733 |
| 2011/0201685 | A1 | | 8/2011 | Campbell | |
| 2013/0052307 | A1 | * | 2/2013 | Elejalde | A23G 1/54 426/93 |
| 2013/0125904 | A1 | * | 5/2013 | Chen | A24B 15/30 131/275 |
| 2013/0316042 | A1 | | 11/2013 | Guan et al. | |
| 2014/0039057 | A1 | | 2/2014 | Campbell | |

FOREIGN PATENT DOCUMENTS

| CN | 1073589 A | 6/1993 |
| CN | 1054523 A | 5/1997 |
| CN | 1479579 A | 3/2004 |
| CN | 102131496 A | 7/2011 |
| WO | 2011/163152 A1 | 12/2011 |

OTHER PUBLICATIONS

Sigma-Aldrich—"Particle Size Conversion Table." Retrieved on Jul. 25, 2016. Retrieved from the internet <URL: http://www.sigmaaldrich.com/chemistry/stockroom-reagents/learning-center/technical-library/particle-size-conversion.html>.*

* cited by examiner

Primary Examiner — Doan T Phan
(74) Attorney, Agent, or Firm — McNees Wallace & Nurick LLC

(57) ABSTRACT

A comestible article is disclosed that employs finely ground demulcent particles of a median particle size such that the demulcent is not readily perceived by the human tongue and in which the demulcent granules are not fully hydrated. As a result of the small particle size and lack of being fully hydrated during production, the demulcent particles exhibit faster and greater levels of hydration upon consumption, leading to quicker and more complete relief.

18 Claims, 3 Drawing Sheets

COMESTIBLE CONTAINING FINELY GROUND DEMULCENT

CROSS REFERENCE TO RELATED APPLICATION

This application claims the benefit of and priority to U.S. Provisional Application No. 61/813,209, filed Apr. 18, 2013, which is hereby incorporated by reference in its entirety.

FIELD

The present application is directed toward the field of demulcents and more particularly to comestibles containing demulcents in a form that is not fully hydrated until consumed.

BACKGROUND

When an individual is affected with a sore throat and/or a cough they often seek an item to provide relief. One such item may include a demulcent. Demulcents soothe or soften minor pain and/or inflammation, usually through formation of a film over a mucous membrane.

One type of demulcent includes pectin, which may be delivered in demulcent throat soothers such as hard candy, chewy candy, or gummies. However, current methods for forming throat soothers including pectin or other demulcents require pre-hydration generally involving the addition of water, processing of hydrated pectin granules, and subsequent dehydration. Additionally, current methods of employing pectin for use as a demulcent is believed to rely upon particles 100 microns or larger, which is the size at which pectin is generally commercially available.

What is needed is a comestible containing a demulcent that does not require pre-hydration for item formation, does not contain demulcent particles perceivable by the individual's tongue, and has a rapid hydrolysis resulting in quicker soothing benefits.

SUMMARY

Exemplary embodiments are directed to comestibles that contain or have a coating that contains a finely ground demulcent that does not require pre-hydration and that exhibits faster, more complete relief when consumed.

In one embodiment, a comestible comprises a sweetener and demulcent granules having a particle size such that the demulcent is not perceived by the human tongue, wherein the demulcent granules are not fully hydrated.

In one embodiment, the comestible comprises a pressed tablet comprising a sweetener selected from the group consisting of sorbitol, mannitol, maltitol, erythritol, xylitol, isomalt, lactitol and combinations thereof, and 0.3% to 5% by weight pectin granules having a median particle size less than 50 microns, wherein the pectin granules are not fully hydrated.

Embodiments may employ other types of comestibles, sweeteners, and demulcents all as more fully described herein.

In another embodiment, a method of forming a comestible comprises providing demulcent granules having a maximum average particle size such that the demulcent is not perceived by the human tongue, combining the demulcent granules with a sweetener and processing the sweetener and demulcent granules to form a comestible wherein the processing results in a comestible in which the demulcent granules are not fully hydrated upon formation of the comestible.

Yet another embodiment of the invention is directed to providing the comestibles described herein containing an effective amount of the demulcent granules to provide sore throat relief and in which the demulcent granules become fully hydrated upon ingestion.

An advantage of exemplary embodiments is that the use of a finely ground demulcent allows the inclusion of the delmucent without the need for pre-hydrating it in advance, saving time and costly manufacturing steps associated with subsequent de-hydration.

Another advantage is that when the tablet or other comestible is consumed, the finely ground demulcent hydrates directly in the consumer's mouth.

Other features and advantages of the present invention will be apparent from the following more detailed description of exemplary embodiments that illustrate, by way of example, the principles of the invention.

DETAILED DESCRIPTION OF EXEMPLARY EMBODIMENTS

Figure 1:
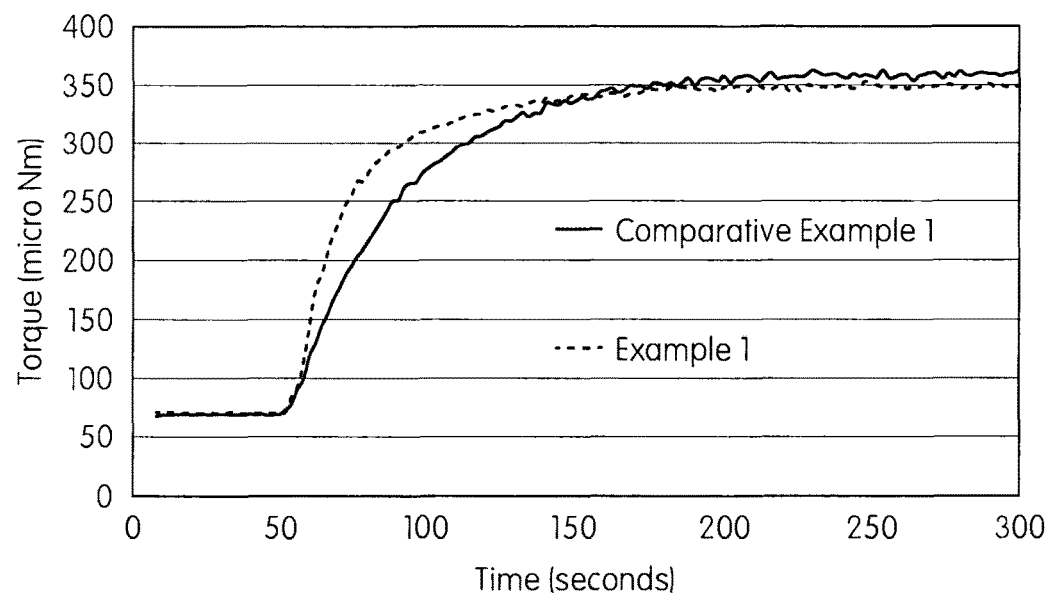
FIGS. 1-6 graphically illustrate experimentally determined torque and hydration rate measurements.

Exemplary embodiments are directed to incorporation of a finely ground demulcent in a comestible, such as a compressed tablet, and/or a coating having a low moisture content. The use of a finely ground demulcent allows the inclusion of the delmucent without the need for pre-hydrating it in advance, saving time and costly manufacturing steps associated with subsequent de-hydration so that when the tablet or other object is consumed, the finely ground demulcent hydrates directly in the consumer's mouth.

Particle size, as used herein, refers to the median particle size of the demulcent particles employed. Exemplary embodiments make use of finely ground particles having a particle size of 50 microns or less when pectin is employed as the demulcent. That is, 50% of the particles have a size that is 50 microns or less. In one embodiment, the particle size is 35 microns or less. In certain preferred embodiments, the particle size is 25 microns or less. Pectin particles of 50 microns or less generally corresponds to the minimum size at which a human tongue is able to perceive the pectin when incorporated into the comestible. While primarily described herein with respect to pectin as the demulcent, it will be appreciated that the invention is not so limited and that other demulcents may be employed and that the corresponding particle size used may vary depending upon the composition and/or amount of the demulcent, in that some demulcents may be less detectable by the tongue at slightly larger particle sizes or because of the small amount used. For example, certain hydrocolloids may not be perceived by the tongue at median particle sizes of up to 75 microns or larger.

The finely ground demulcent may be formed through a single stage grinding process, or a multiple stage grinding process. The single stage grinding process may be suitable for demulcent granules having an initial particle size of less than 200 microns, as commercially available pectins can be obtained in the range of 100 to 200 microns median particle size. During grinding, the size of the demulcent granule may be reduced by up to 75% in a single pass. For demulcent granules having a size of greater than about 200 microns, the multiple stage grinding process may be required. The multiple stage grinding process further reduces the size of the demulcent granule with each pass, so that granules having sizes greater than 200 microns may go through multiple passes to form the finely ground demulcent.

The larger granule size demulcent is finely ground using any suitable grinding mechanism, such as a grinding mill. Suitable grinding mills include, but are not limited to a rotor mill, a mixer mill, a planetary ball mill, a jet mill, ajar mill, or a combination thereof. Different grinding mills and/or a different starting size of the granule produce different sizes of the finely ground granule. Repeated grinding may further reduce the granule size. In an exemplary embodiment, the demulcent granules do not clump or stick together during the grinding, substantially eliminating detectable groupings of granules in the final comestible. The grinding may be completed when the desired average particle size of the granules is reached; while exemplary embodiments are primarily directed to any size finely ground (i.e., less than 50 microns) demulcent, particle sizes of about 25 microns or less are generally preferred particularly for coating applications because they can be incorporated without being readily discernible by the tongue. Furthermore, the larger the particle size, the longer it generally takes to fully hydrate, which can delay the demulcent's soothing benefit.

Reducing the size of the demulcent granules decreases the tongues ability to perceive each granule and increases the surface area as compared to the same volume of the demulcent having larger granule sizes. Unlike current production methods, the finely ground demulcent granules are not fully hydrated, such as by dissolving in water or other aqueous solution. Instead, the finely ground granules are incorporated directly into the final product such that when consumed, they fully hydrate directly into the saliva of the consumer, forming a demulcent film having a viscosity suitable for coating a membrane. In one embodiment, the demulcent granules are not pre-hydrated at all when introduced into the comestible, although it will be appreciated that certain comestible compositions and/or certain environments to which the comestible is exposed may result in some hydration prior to consumption. In any event, exemplary embodiments do not exhibit full hydration of the demulcent until consumed.

The increased surface area of the finely ground demulcent contributes to an increased rate of hydration. The increased rate of hydration increases the rate at which the finely ground demulcent granules form the viscous demulcent film, which provides temporary relief from minor pain/inflammation. As a result, the increased rate of formation can decrease the time between the hydration and the relief.

A preferred demulcent for use in exemplary embodiments is pectin. Other suitable demulcents include any mouth feel agent that imparts a soothing effect, typically by imparting greater viscosity characteristics to saliva that results in a viscous film that coats the oral cavity and throat, including hydrocolloids. Exemplary demulcents include, but are not limited to, coltsfoot, comfrey, common purslane, corn silk, couchgrass, dead nettle, flaxseed, irish moss, lungwort, loquat, mallow, marshmallow, mullein, oatmeal, parsley piert, plantain, slippery elm, xanthan gum, carrageenan, konjac, psyllium, fenugreek gum, propylene glycol alginates, guar gum, gum acacia, cellulose gum, locust bean gum, citrus fiber, tara gum, sodium alginate, gum tragacanth, agar agar, and combinations of the foregoing.

The pectin or other demulcent can be incorporated into the comestible and/or a coating applied to a coated comestible. The types of comestibles into which the fine demulcent granules are incorporated is not limited except for those whose method of manufacture would involve exposing the demulcent to sufficient amounts of moisture that would result in full hydration of the demulcent during the manufacturing process. Suitable comestibles include pressed tablets, mints, pills, tablets, chewing gum, licorice, hard candy and chewy candy (including solid hard or chewy candy centers, as well as hard or chewy candy shells surrounding another candy or liquid or gel center), dissolvable tablets or films, and constructions that employ combinations of any one or more of the foregoing, all by way of example.

In one embodiment, the comestible is a sugar base pressed tablet, while in another embodiment the pressed tablet has a polyol base, such as, but not limited to, sorbitol, maltitol, erythritol, mannitol, xylitol, isomalt, lactitol and combinations of these materials.

Additionally, other ingredients may be incorporated into the comestible to provide flavoring or other enhancements to the sensory profile delivered. Additives that contribute to the sensory profile include those which alter the flavor, texture, taste, sensation, or intensity.

Thus, exemplary additives include flavorants to impart a flavor to the comestible composition, sensates which may contain acids or other active ingredients to deliver a sensation, such as coolness, hotness, tingling, effervescence, and salivation, by way of example only, and tastants that impart tastes such as, bitter, salty, sweet, sour, umami and kokumi tastes.

Flavorants can be any natural or synthetic flavoring agents known in the food art and may be selected from synthetic flavor oils and flavoring aromatics, and/or oils, oleo resins and extracts derived from plants, leaves, flowers, fruits and the like. Combinations of these materials may also be used. In certain embodiments, flavorants may be employed to impart or enhance green tea flavor in conjunction with the presence of the green tea polyphenol compounds. Other exemplary flavors include, but are not limited to, spearmint oil; cinnamon oil; oil of wintergreen (methylsalicylate); peppermint oil; clove oil; bay oil; anise oil; eucalyptus oil; thyme oil; cedar leaf oil; oil of nutmeg; oil of sage; oil of bitter almonds; cassia oil; citrus oil (e.g., lemon, lime, orange, grapefruit, etc.); grape oil; natural and synthetic flavorings like vanilla, cocoa and caramel; and fruit essences such as apple, banana, pear, peach, strawberry, raspberry, cherry, plum, pineapple, and apricot all by way of example only.

The flavorant may be an oil or liquid base composition and powdered flavorants may also be used. While the comestible composition contains a flavorant in most embodiments, it will be appreciated that flavoring is not required and that a particular comestible composition containing a finely ground demulcent in accordance with exemplary embodiments could also be flavor neutral.

Sensate compounds can include cooling agents, warming agents, tingling agents, effervescent agents, salivating agents and combinations thereof. Any food-grade acids or other ingredients known in the art for inducing a sensation when consumed can also be used. Exemplary such materials include, but are not limited to, citric acid, succinic acid, fumaric acid, malic acid and tartaric acid. Other exemplary sensate ingredients include menthol, xylitol, erythritol, dextrose, sorbitol, and mannitol can be used to impart a cool sensation due to negative heat of solution. Flavoring components that may also impart a cooling sensation include menthane, menthone, ketals, menthone ketals, menthone glycerol ketals, substituted p-menthanes, acyclic carboxamides, mono menthyl glutarate, substituted cyclohexanamides, substituted cyclohexane carboxamides, substituted ureas and sulfonamides, substituted menthanols, hydroxymethyl and hydroxymethyl derivatives of p-menthane, 2-mercapto-cyclo-decanone, hydroxycarboxylic acids with 2-6 carbon atoms, cyclohexanamides, menthyl acetate, menthyl salicylate, N,2,3-trimethyl-2-isopropyl butanamide (WS-23), N-ethyl-p-menthane-3-carboxamide (WS-3), isopulegol, 3-(1-menthoxy)propane-1,2-diol, 3-(1-menthoxy)-2-methylpropane-1,2-diol, p-menthane-2,3-diol, p-menthane-3,8-diol, 6-isopropyl-9-methyl-1,4-dioxaspiro[4,5]decane-2-methanol, menthyl succinate and its alkaline earth metal salts, trimethylcyclohexanol, N-ethyl-2-isopropyl-5-methylcyclohexanecarboxamide, Japanese mint oil, peppermint oil, 3-(1-menthoxy)ethan-1-ol, 3-(1-menthoxy)propan-1-ol, 3-(1-menthoxy)butan-1-ol, 1-menthylacetic acid N-ethylamide, 1-menthyl-4-hydroxypentanoate, 1-menthyl-3-hydroxybutyrate, N,2,3-trimethyl-2-(1-methylethyl)-butanamide, n-ethyl-t-2-c-6 nonadienamide, N,N-dimethyl menthyl succinamide, substituted p-menthanes, substituted p-menthane-carboxamides, 2-isopropanyl-5-methylcyclohexanol (from Hisamitsu Pharmaceuticals, hereinafter "isopregol"); menthone glycerol ketals (FEMA 3807, tradename FRESCOLAT® type MGA); 3-1-menthoxypropane-1,2-diol (from Takasago, FEMA 3784); and menthyl lactate; (from Symrise, FEMA 3748, tradename FRESCOLAT® type ML), WS-30, WS-14, eucalyptus extract (p-mehtha-3,8-diol), menthol (its natural or synthetic derivatives), menthol propylene glycol carbonate, Menthol ethylene glycol carbonate, Menthol glyceryl ether, N-tertbutyl-p-menthane-3-carboxamide, P-menthane-3-carboxylic acid glycerol ester, methyl-2-isopropyl-bicyclo(2.2.1), heptane-2-carboxamide; menthol methyl ether, and menthyl pyrrolidone carboxylate among others.

Other sensates include encapsulated products such as those sold under the tradenames Durarome®, Flexarome®, FirCaps® and Popscent®, which may also be used to impart a texture to the comestible composition.

Sweeteners may also be present in the comestible composition and, as noted previously, are typically present as the base composition that forms the matrix of the formed comestible, particularly in non-gum applications. Sweeteners for use in forming the base may include sugars, such as, but not limited to, sucrose, dextrose and combinations of these materials, or polyols, such as, but not limited to, sorbitol, mannitol, maltitol, erythritol, xylitol, isomalt, lactitol and combinations of these materials. In some embodiments, one or more additional, typically intense, sweeteners may also be included to enhance the flavor profile such as acesulfam-K, aspartame, neotame, stevia, and monk fruit extract among others.

Still other additives that may be employed in the comestible composition include colorants, stabilizers and/or preservatives to improve shelf life, and any other additives commonly used in other types of comestible compositions.

Exemplary embodiments are also directed to coated comestibles in which the finely ground demulcent is present in the coating, with the underlying base comestible optionally separately containing or omitting the presence of the finely ground demulcent. When the demulcent is incorporated into the coating, the range of comestible expands further to include non-manufactured comestibles such as fruit and nuts as well as comestibles that are manufactured using large amounts of moisture that would fully hydrate the demulcent such as lozenges, gummies and gels, for example.

For embodiments that include pectin as the finely ground demulcent, both high methoxyl and low methoxyl pectins or a combination may be employed. High methoxyl pectin has an esterification of above 50%, typically in the range of 51 to 75%, while low methoxyl pectin has an esterification of below 50%, typically in the range of 20 to 49%. While it has heretofore been difficult to form candy or other comestibles of any kind using low methoxyl pectin because of its fast gelling effect using traditional methods, exemplary embodiments are not so limited because they do not fully hydrate the pectin in advance, but rather incorporate the pectin directly in a finely ground form.

As a result, in some exemplary embodiments, a compressed tablet or other comestible is formed with the inclusion of low methoxyl pectin, providing a suitable delivery method. As the compressed tablet breaks apart in the mouth, the low methoxyl pectin is hydrated by saliva forming the demulcent film that coats the oral cavity and throat. Low methoxyl pectin may also be used in the formation of a coating for compressed tablets as those coatings are otherwise known in the art. Because the coating may have a higher moisture content than tablets and other base comestibles, in some circumstances low methoxyl pectin may be less desirable than high methoxyl pectin for coating applications.

The amount of demulcent included in the comestible may depend on a variety of factors, including the specific demulcent(s) used and the type of comestible in which it is used. However, the comestible typically contains at least 0.30% by weight of the finely ground demulcent up to 5% by weight. In embodiments in which the demulcent is pectin incorporated into a pressed table, the comestible is generally in the range of 0.3% by weight to 3% by weight pectin. In embodiments in which the demulcent is a hydrocolloid, such as konjica, the comestible is more typically in the range of 0.3% to 1.5% by weight.

The compressed tablet can deliver an equal or greater amount of relief in a decreased time as compared to products using similar amounts of pectin having the larger granule size as well as compared to conventional products manufactured using pre-hydrated pectin.

In embodiments in which pectin is employed in a tablet coating (which may be used in combination with compressed tablets that either do or do not also employ a finely ground pectin), the coating may be formulated to deliver up to 10 milligrams of pectin and typically in the range of 3 to 10 milligrams of pectin.

Neither the formation of the compressed tablet nor the formation of the coating require pre-hydration of the pectin. As a result, the cost of production can be decreased by eliminating the pre-hydration step, along with other processing and re-hydration steps used for currently available products. The elimination of the pre-hydration, processing, and re-hydration steps reduces manufacturing time in addition to cost.

The invention is further described in conjunction with the following non-limiting examples that are provided to illustrate the principles of the invention.

EXAMPLES

Example 1

2.4 grams of sorbitol was blended with 0.6 grams of high methoxyl pectin powder in which the pectin had been finely ground to a particle size in which 83% of the particles were less than 45.5 microns. Agglomerates were broken by careful hand mixing.

20 mL of deionized water was added to a steel container of a rheometer (Rheolyst, model AR1000-N, TA Instruments). The water was maintained at between 37-39 degrees Celsius. The height of the vane used was calibrated by zeroing the gap, and the gap between the vane and bottom surface of the steel container was kept to a height of 1000 micrometer. The rheometer's measurement was started with the vane rotating at an angular velocity of 100 radians per second. At the 50th second, the blend of sorbitol and pectin was injected using a syringe and torque was measured until the 300th second.

Comparative Example 1

A comparative example was formulated in the same way as Example 1, except that the pectin was left in its commercially available granule size, in which the 90% size was 231 microns and the 50% size was 118 microns (i.e., greater than 90% had a size less than 231 microns and greater than 50% had a size less than 118 microns). The torque was measured in the same manner as described in Example 1.

Figure 2:
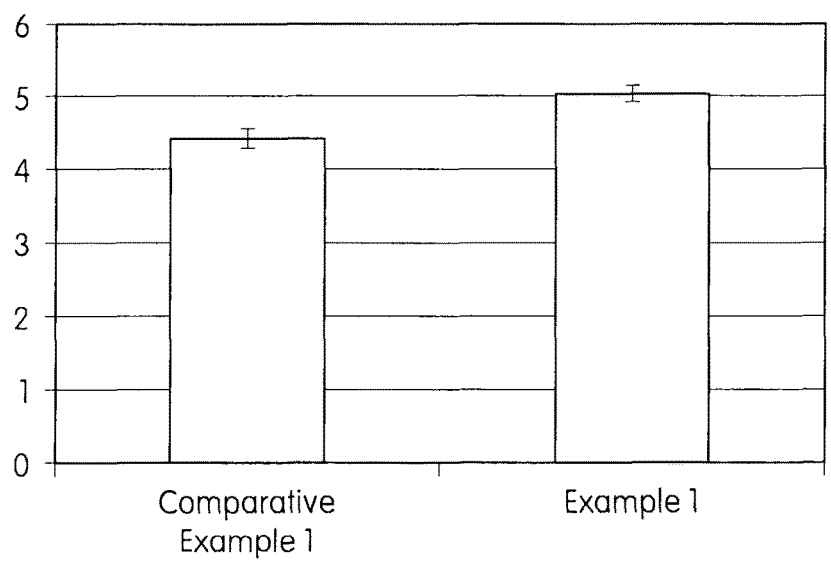

FIG. 1 illustrates the torque of the two blends, while FIG. 2 graphically illustrates hydration rate of the two different sizes of pectin and demonstrates the enhanced hydration rate that results from the use of the finely ground high methoxyl pectin. Hydration rate was calculated by comparing the slopes of the torque curve at the 50th and 100th seconds.

Example 2

A blend was made in the same manner as Example 1, except that a low methyoxl pectin was employed. The low methoxyl pectin was ground from its obtained form with a median particle size of 89 microns, 83% below 179 microns to a median particle size of 12 microns, with 83% less than 23 microns. The torque was measured in the same manner described for Example 1.

Comparative Example 2

A second comparative example was formulated in which the low methoxyl pectin was left in its commercially available median granule size of 89 microns. The torque was again measured in the same manner as the others.

Comparative Example 3

A third comparative example was formulated as a sorbitol blank in which the full 3 g mass was sorbitol with no added pectin, with torque again measured in the same way.

Figure 3:
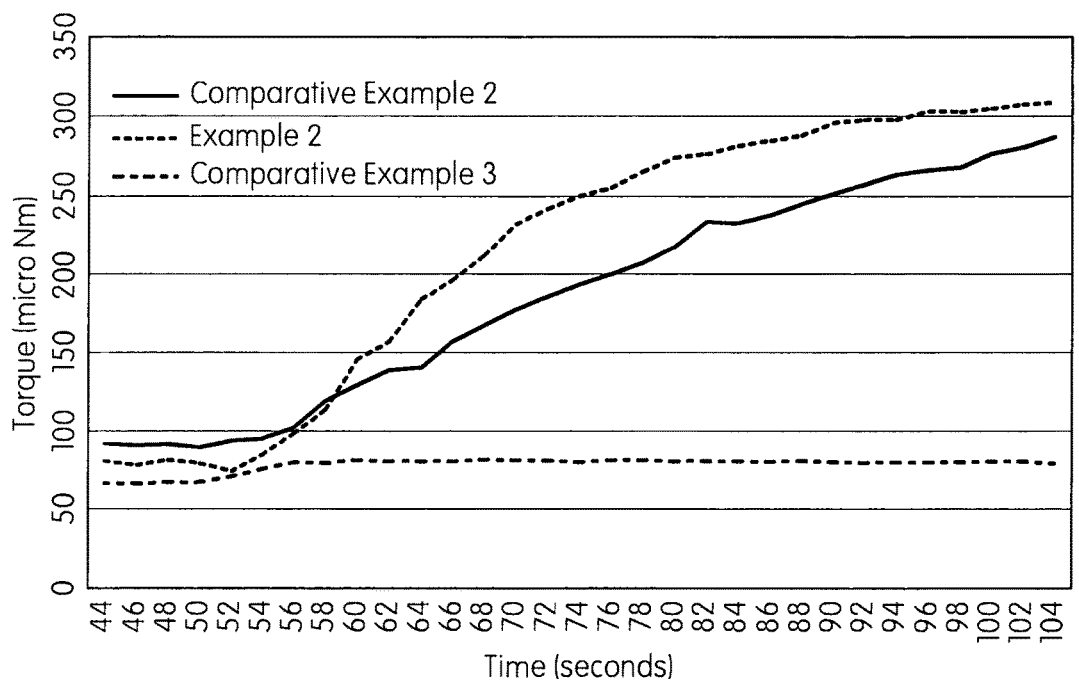
Figure 4:
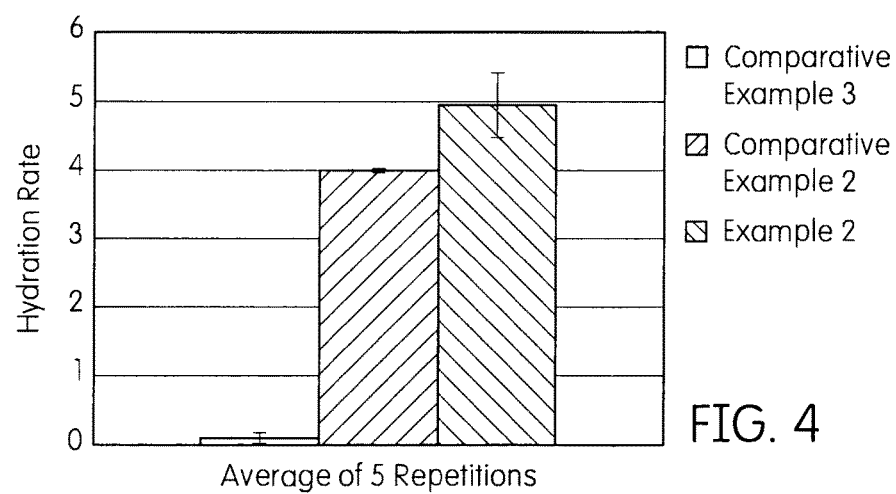

FIG. 3 illustrates the torque of the two blends and the control, shown over the range of 44 to 104 seconds, to more readily illustrate the period when most of the change is occurring. FIG. 4 graphically illustrates hydration rate, calculated in the way previously described, of the three different samples and again demonstrates the enhanced hydration rate that results from the use of the finely ground low methoxyl pectin.

Examples 4 and 5

A commercially available konjac gum (103 micron median particle size), a hydrocolloid, was shear milled to 69 micron median particle size (Example 4) and to 23 micron median particle size (Example 5). The konjac gum was then blended at 0.75% by weight into sorbitol and the torque was measured in the manner previously described.

Comparative Examples 4 and 5

Comparative examples were formulated using the unground konjac gum (Comparative Example 4) and a sorbitol blank containing no konjac gum (Comparative Example 5). The torque was measured in the same manner as described.

Figure 5:
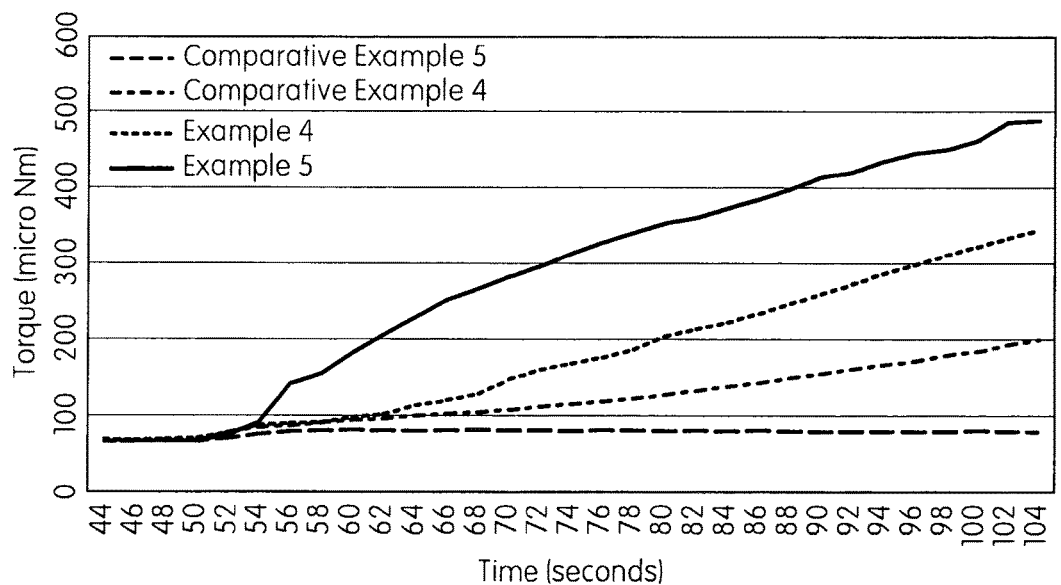
Figure 6:
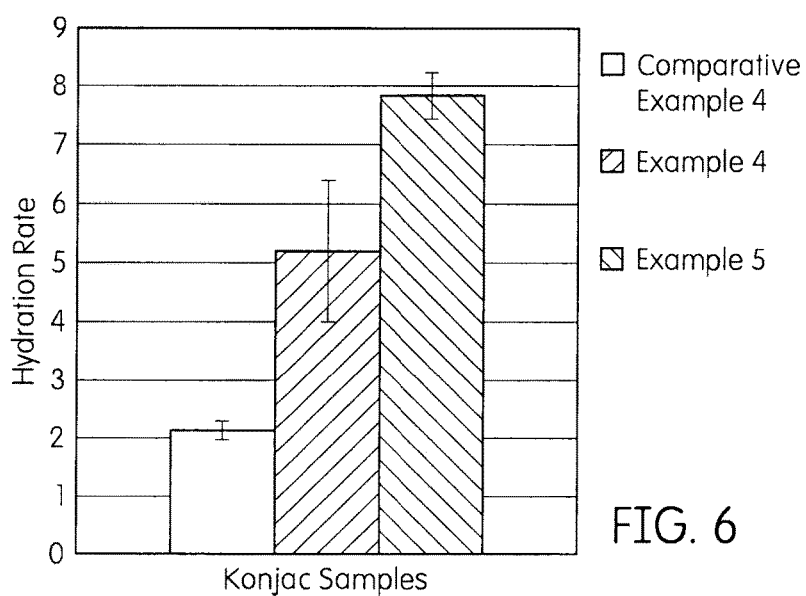

FIG. 5 illustrates the torque of the two blends and the two comparative samples, again shown over the range of 44 to 104 seconds, to more readily illustrate the period when most of the change is occurring. FIG. 6 graphically illustrates hydration rate. As before, enhanced hydration rate that results from the use of the finely ground versions of the konjac gum, with particularly significant enhancement of the 23 micron particle size of Example 5.

Example 6

The commercially available high methoxy pectin used in Example 1 was jet milled from its original size to reduce the particle size to a median of 32 microns, with a 90% size of 82 microns. No clumping or sticking was observed during milling. Sample tablets were prepared using 0.3% by weight and 1.0% by weight of the finely ground pectin, in which the finely ground pectin was compounded with sorbitol, magnesium stearate, sweetener, and flavorings and then formed into compressed tablets 13 mm in diameter having a total weight 0.8 grams each.

Example 7

Some of the finely ground pectin used in Example 6 was mixed with xylitol and flavoring and coated onto 0.8 g compressed isomalt tablets to form a coated comestible having a coating weight of approximately 30% (based on the total weight of the coated comestible). Coated comestibles were formulated with coatings having 0.3% by weight and 1.0% by weight of the finely ground pectin.

Example 8

Some of the finely ground low methoxyl pectin of Example 2 was reserved and mixed with sorbitol, magnesium stearate, sweetener and flavorings and formed into fruit flavored mints of a similar shape and weight as those in Example 6. Samples were made containing 1%, 5%, and 10% by weight of the pectin.

Example 9

A similar pectin to that used in Example 6 was added into a compressed mint formulation at 1% by weight in combination with 0.5% of a commercially available xanthan gum which was unground (but undetectable as consumed at that level). These tablets were produced with typical processing parameters in both fruit and mint versions, the tablets being 20 mm in diameter and 1.8 g total weight.

Example 10

The finely ground konjac gum of Examples 4 and 5 are made into pressed tablets at 0.75% by weight konjac gum.

While the invention has been described with reference to particular embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims and all other patentable subject matter contained herein.

The invention claimed is:

1. An article comprising:
   a formed comestible consisting of:
   a base composition consisting of at least one sweetener; and
   a plurality of granules consisting of at least one demulcent, the plurality of granules having a median particle size of about 75 microns or less such that the demulcent is not perceived by the human tongue, wherein the at least one demulcent is not fully hydrated in the formed comestible.

2. The article of claim 1 further comprising a coating on the formed comestible.

3. The article of claim 1, wherein the at least one demulcent comprises pectin.

4. The article of claim 3, wherein the pectin is high methoxyl pectin.

5. The article of claim 3, wherein the pectin is low methoxyl pectin.

6. The article of claim 3, wherein the at least one demulcent further comprises a hydrocolloid.

7. The article of claim 3, wherein the median particle size of the granules is about 50 microns or less.

8. The article of claim 7, wherein the median particle size of the granules is about 25 microns or less.

9. The article of claim 1, wherein the at least one demulcent comprises a hydrocolloid.

10. The article of claim 1, wherein the demulcent comprises a composition selected from the group consisting of coltsfoot, comfrey, common purslane, corn silk, couchgrass, dead nettle, flaxseed, irish moss, lungwort, loquat, mallow, marshmallow, mullein, oatmeal, parsley piert, plantain, slippery elm, xanthan gum, carrageenan, konjac, psyllium, fenugreek gum, propylene glycol alginates, guar gum, gum acacia, cellulose gum, locust bean gum, citrus fiber, tara gum, sodium alginate, gum tragacanth, agar, and combinations thereof.

11. The article of claim 1, wherein the demulcent is present in an amount in the range of 0.3% to 5% by weight of the formed comestible.

12. The article of claim 1, wherein the comestible is selected from the group consisting of a pressed tablet, a mint, a pill, a tablet, a hard candy, a chewy candy, a dissolvable tablet, and a dissolvable film.

13. A comestible comprising:
    a pressed tablet consisting of:
    at least one sweetener selected from the group consisting of sorbitol, mannitol, maltitol, erythritol, xylitol, isomalt, lactitol, and combinations thereof; and
    a plurality of granules consisting of at least one demulcent in an amount in the range of 0.3% to 5% by weight of the pressed tablet, the plurality of granules being blended with the at least one sweetener, the at least one demulcent comprising pectin, and the plurality of granules having a median particle size less than 50 microns, wherein the at least one demulcent is not fully hydrated in the pressed tablet.

14. The comestible of claim 13, wherein the pectin comprises low methoxyl pectin.

15. The comestible of claim 13, wherein the pectin granules are present in an amount in the range of 0.3% to 1% by weight of the pressed tablet.

16. The comestible of claim 13, wherein the at least one demulcent further comprises a hydrocolloid.

17. The article of claim 1, wherein the demulcent is not pre-hydrated in the plurality of granules.

18. The comestible of claim 13, wherein the comestible consists of the at least one sweetener and the plurality of granules.

* * * * *